United States Patent [19]

Still et al.

[11] Patent Number: 5,571,911
[45] Date of Patent: Nov. 5, 1996

[54] METHOD OF PURIFYING ORGANIC COMPOUNDS USING AN ENANTIOSELECTIVE RECEPTOR

[75] Inventors: W. Clark Still, New York, N.Y.; Julian A. Simon; Jong-In Hong, both of Cambridge, Mass.

[73] Assignee: The Trustees of Columbia University in the City of New York, New York, N.Y.

[21] Appl. No.: 296,814

[22] Filed: Aug. 26, 1994

Related U.S. Application Data

[62] Division of Ser. No. 901,401, Jun. 19, 1992, Pat. No. 5,342,934.

[51] Int. Cl.$^6$ .................. C07D 487/18; C07D 513/18; C07D 498/18; C07B 57/00
[52] U.S. Cl. ................ 540/456; 540/460; 560/18; 560/25
[58] Field of Search .................. 540/456, 460

[56] References Cited

U.S. PATENT DOCUMENTS

| | | | |
|---|---|---|---|
| 4,043,979 | 8/1977 | Cram | 260/47 UP |
| 4,128,556 | 12/1978 | Cram | 546/26 |

OTHER PUBLICATIONS

Borchardt, A., Still, W. C., Synthetic Receptor Binding Elucidated with an Encoded Combinatorial Library, *J. Am. Chem. Soc.*, 116:373–374 (1994); U.S.A.

Diederich, F., Complexation of Neutral Molecules by Cyclophane Hosts, *Angew. Chem. Int. Ed. Engl.*, 27:362–386 (1988); Germany.

Ebmeyer, F., and Vogtle, F., Selective Molecular Recognition of Trihydroxybenzenes, *Angew. Chem. Int. Ed. Engl.*, 28:79–81 (1989); Germany.

Erickson, S. D., et al., Practical Synthesis of a Highly Enantioselective Receptor for Peptides, *J. Am. Chem. Soc.*, 115:1035–1308 (1993); U.S.A.

Fujita, T. and Lehn, J.–M., Synthesis of Dome–Shaped Cyclophane Type Macrotricyclic Anion Receptor Molecules, *Tetrahedron Letters*, 29(14):1709–1712 (1988); G.B.

Garrett, T., et al., Synthesis and Characterization of Macrobicyclic Iron (III) Sequestering Agents, *J. Am. Chem. Soc.*, 113:2965–2977 (1991); U.S.A.

Hong, J.–I., et al., Highly Selective Binding of Simple Peptides by a $C_3$ Macrotricyclic Receptor, *J. Am. Chem. Soc.*, 113:5111–5112 (1991): U.S.A.

Jeong. K.–S., et al., Molecular Recognition. Asymmetric Complexation of Diketopiperazines, *J. Am. Chem. Soc.*, 112:6145–6146 (1990); U.S.A.

Liu, R. and Still, W. C., Highly Selective Binding of Diverse Neutral Donor/Acceptor Substrates . . . , *Tetrahedron Lett.*, 34 (16):2573–2576 (1993); Great Britain.

Liu, R., et al., Enantioselective Complexation of the Alanine Dipeptide by a $C_2$ Host Molecule, *J. Org. Chem.*, 55:5184–5186 (1990); U.S.A.

Murakami, T., et al., Capped Azaparacyclophane, *J. Chem. Soc.*, Chem. Commun., 753–755 (1985); Great Britain.

Sanderson, P. E. J., et al., Enantioselective Complexation of Simple Amides by a $C_2$ Host Molecule, *J. Am. Chem. Soc.*, 111:8314–8315 (1989); U.S.A.

Wambach, L., and Vogtle, F., Tetrahydrofuran–Einschluss und Gast–Selektive Katalyse des H/D Austauschs in Saurer Losung, *Tetrahedron Letters*, 26:1483–1486 (1995); G.B.

Yoon, S. S. and Still, W. C., An Exceptional Synthetic Receptor for Peptides, *J. Am. Chem. Soc.*, 115:823–824 (1993); U.S.A.

Yoon, S. S., and Still, W. C., Cyclooligomeric Receptors for the Sequence Selective Binding of Peptides. *Tetrahedron Letters* 35:8557–8560 (1994); Great Britain.

*Primary Examiner*—Mukund J. Shah
*Assistant Examiner*—Pavanaram K. Sripada
*Attorney, Agent, or Firm*—John P. White

[57] ABSTRACT

The present invention relates to a composition having the general formula:

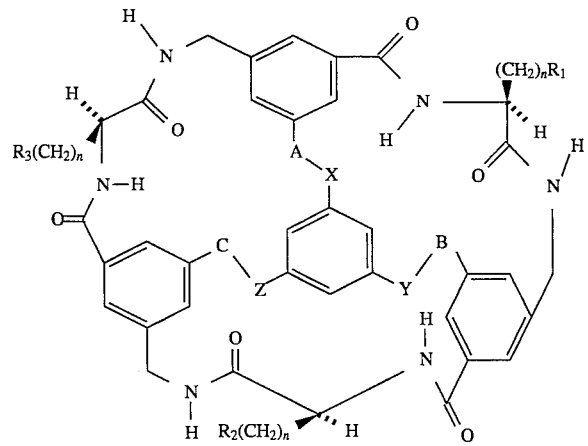

wherein each of A, B, C, X, Y, and Z is independently O, NH, N(CH$_2$)$_m$CH$_3$, N(C=O) (CH$_2$)$_m$CH$_3$, CH$_2$, S, or Se; each of R$_1$, R$_2$, and R$_3$ is independently phenyl, 4-hydroxyphenyl, pyridyl, pyrrolyl, indolyl, naphthyl, thiophenyl, (C=O) (CH$_2$)$_p$CH$_3$, NH(C=O) (CH$_2$)$_p$CH$_3$, OH, COOH, NH$_2$, or SH; and m, n, and p are integers between 0 and 5. The composition is a chiral receptor molecule useful for the purification of enantiomers of derivatives of amino acids and of compounds able to form hydrogen bonds. The preparation of the composition involves coupling a trifunctional aromatic molecule with three protected chiral molecules at the three aromatic groups, cleaving protecting groups, and joining adjacent chiral groups by multiple lactamizations. The receptor may be used in a form either bound to a solid support or dissolved in an immiscible phase to effect convenient purification of enantiomers or other compounds of interest.

2 Claims, No Drawings

METHOD OF PURIFYING ORGANIC COMPOUNDS USING AN ENANTIOSELECTIVE RECEPTOR

This invention was made with government support under grants #GM-44525 and #CHE89-11008 from the National Institutes of Health and the National Science Foundation, respectively. Accordingly, the U.S. Government has certain rights in the invention.

This application is a divisional of U.S. Ser. No. 07/901,401 filed Jun. 19, 1992, now U.S. Pat. No. 5,342,934 the contents of which are hereby incorporated by reference.

BACKGROUND OF THE INVENTION

This invention relates to the field of molecular recognition of small ligands. More particularly, the invention relates to compositions useful for the purification of enantiomers of amino acid derivatives and for the purification of certain amino acids able to form hydrogen bonds, methods for preparing these compositions, and methods for using them.

Standard approaches to the optical resolution and purification of organic and biological molecules include crystallization, distillation, extraction, and chromatography (Eliel, *Stereochemistry of Carbon Compounds*, New York: McGraw-Hill, 1962). Each methodology is based on a physical or chemical interaction of a molecule with an element of its environment, and may involve molecular sizing, electrostatics, hydrophobicity, sterics, or polarity. The efficiency of purification increases as the differences in interaction energy for all the species present in the mixture increase. The relevant interactions for crystallization are crystal lattice forces and solvation of the molecule; for distillation, the interaction is a liquid-gas phase transition; while for extraction and chromatography, the interaction is exchange between non-miscible phases. Common to all these classic methods is the limitation that as molecular structures become increasingly similar, the energy differentials for the relevant interaction diminish to the extent that high resolution is no longer feasible. A general approach to purification necessitates an enhanced capability for transcending this natural tendency toward shrinking energy differences. The ability to purify very similar or chiral molecules is of economic and practical importance to the developing fields of biotechnology, and should greatly accelerate the development of new pharmaceuticals and bioactive and other useful compounds.

The ability to distinguish similar molecules is an important goal of research in the field of molecular recognition. Early efforts to bind molecules selectively involved naturally occurring host molecules, such as clathrates, cholic acid, and cyclodextrins (Diederich, *Anew. Chem. Int. Ed. End.*, 27, 362 (1988); Breslow, *Science (Washington, D.C.)*, 218, 532 (1982)). The first example of a synthetic system specifically designed to undergo inclusion complexation was a cyclophane (Stetter & Roos, *Chem. Ber.*, 88, 1390 (1955)). Synthetic crown ethers and cyclic polyamines were designed to complex metal ions selectively by adjusting ring size and number of heteroatoms (Pederson, *Angew. Chem. Int. Ed. Eng.*, 16, 16 (1972)). Macrobicyclic compounds have been prepared which show selectivity for trihydrobenzenes with certain substitution patterns (Ebmeyer and Vogtle, *Angew. Chem. Int. Ed. Engl.*, 28, 79 (1989)).

The use of chiral components in constructing host compounds has led to the development of molecules which are, in principle, capable of diastereoselective complexation with chiral guests. While several systems have exhibited some diastereoselectivity, numerous attempts to produce chiral hosts have not produced any known compounds of practical utility prior to the present invention. The earliest preparations of chiral crown amino ethers were applied to cation complexation, and not to chiral discrimination by diastereoselective complexation (Wudl & Gaeta, *J. Chem. Soc., Chem. Commun.*, 107 (1972)). Chiral hosts based on biphenylmacrocycles have shown promise (Kyba, et al., *J. Amer. Chem. Soc.*, 100, 4555 (1978)). A recent example intended to distinguish enantiomers of amino acids and arylpropionic acids however appears from binding studies not to function as a host for nonpolar molecules (Rubin, et al., *J. Org. Chem.*, 51, 3270 (1986)).

High enantioselectivity has thus largely eluded prior workers in the field. A bilaterally symmetric host containing two diiodotyrosine moieties was one of the first to exhibit a measurable difference in binding energy with mirror image guest molecules (Sanderson, et al., *J. Amer. Chem. Soc.*, 111, 8314 (1989)); free energy differences ranged from −0.15 to 0.48 kcal/mole, with binding site saturations up to 67%. More recently, a related chiral host was made with pyridyl moieties replacing benzene rings in the macrocycle, which showed free energy differences up to about 1 kcal/mole and a range of binding saturations of approximately 40–80% (Liu, et al., *J. Org. Chem.*, 55, 5184 (1990)). Chiral hosts in which the enantioselection energies exceed 1 kcal/mole have been virtually nonexistent prior to the present invention.

Progress toward a completely chemoselective or enantioselective host has been limited, proceeding roughly in parallel with growing understanding of intermolecular interactions controlling binding affinity in natural receptors like enzymes and hormone receptors. The present invention provides a composition of matter which possesses enzyme-like enantioselectivity which is sufficiently high to offer practical utility in optical resolution and chemical purification of organic compounds.

SUMMARY OF THE INVENTION

The present invention relates to a composition of matter having the structure:

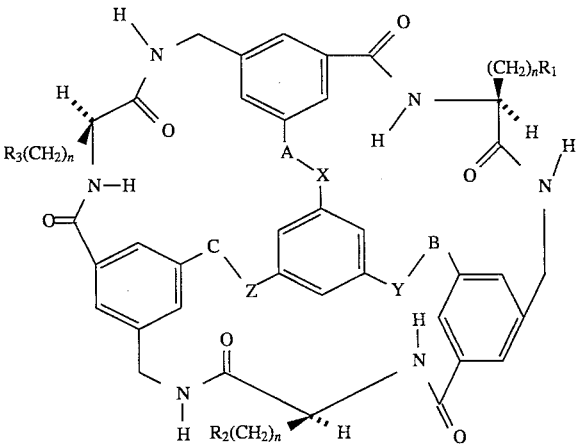

wherein each of A, B, C, X, Y, and Z is independently O, NH, N(CH$_2$)$_m$CH$_3$, N(C=O) (CH$_2$)$_m$CH$_3$, CH$_2$, S, or Se; each of R$_1$, R$_2$, and R$_3$ is independently phenyl, 4-hydroxyphenyl, pyridyl, pyrrolyl, indolyl, naphthyl, thiophenyl, (C=O) (CH$_2$)$_p$CH$_3$, NH(C=O) (CH$_2$)$_p$CH$_3$, OH, COOH, NH$_2$, or SH; and m, n, and p are integers between 0 and 5.

The invention provides a process of obtaining a purified enantiomeric isomer of a compound of interest from a mixture of isomers of such compounds which comprises contacting the mixture of isomers with the composition under conditions such that the enantiomeric isomer binds to the composition plex, separating the resulting complex from the mixture, treating the complex so as to separate the enantiomeric isomer from the composition, and recovering the purified enantiomeric isomer.

The invention also provides a process of obtaining a purified organic compound of interest able to form hydrogen bonds from a mixture of organic compounds which comprises contacting the mixture with the composition under conditions such that the organic compound binds to the composition to form a complex, separating the resulting complex from the mixture, treating the complex so as to separate compound from the composition, and recovering the purified compound.

The invention further provides a process of preparing the composition which comprises: (a) reacting a chiral multi-functional reagent containing at least one protecting group with a compound having the structure:

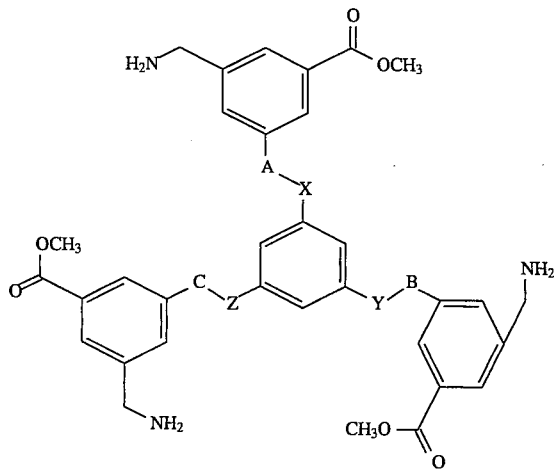

wherein each of A, B, C, X, Y, and Z is independently O, NH, $N(CH_2)_m CH_3$, $N(C=O)(CH_2)_m CH_3$, $CH_2$, S, or Se, under conditions permitting formation of a compound having the structure:

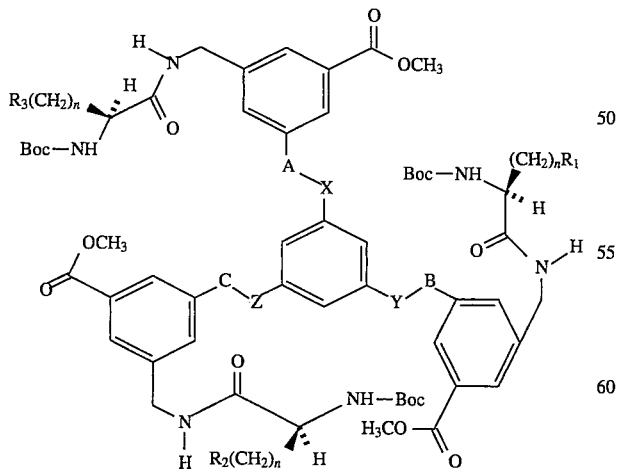

wherein each of A, B, C, X, Y, and Z is independently O, NH, $N(CH_2)_m CH_3$, $N(C=O)(CH_2)_m CH_3$, $CH_2$, S, or Se; each of R, $R_1$, $R_2$, and $R_3$ is independently phenyl, 4-hydroxyhenyl, pyridyl, pyrrolyl, inclolyl, naphthyl, thiophenyl, $(C=O)(CH_2)p CH_3$, $NH(C=O)(CH_2)_p CH_3$, OH, COOH, $NH_2$ or SH; and m, n, and p are integers between 0 and 5;

(b) treating the compound formed in step (a) under suitable conditions so as to cleave one protecting group and form a compound having he structure:

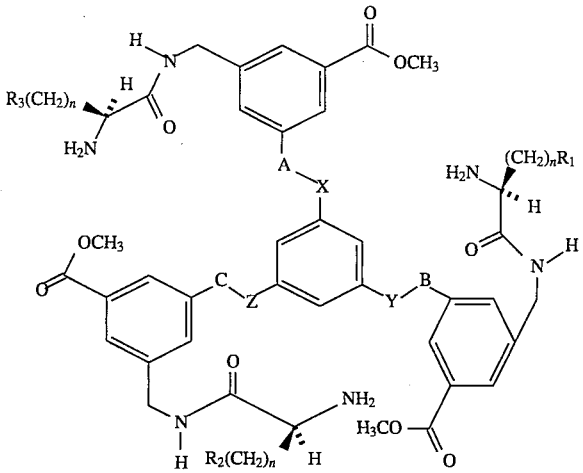

wherein each of A, B, C, X, Y, and Z is independently O, NH, $N(CH_2)_m CH_3$, $N(C=O)(CH_2)_m CH_3$, $CH_2$, S, or Se; each of $R_1$, $R_2$, and $R_3$ is independently phenyl, 4-hydroxyphenyl, pyridyl, pyrrolyl, indolyl, naphthyl, thiophenyl, $(C=O)(CH_2)_p CH_3$, $NH(C=O)(CH_2)_p CH_3$, OH, COOH, $NH_2$, or SH; and m, n, and p are integers between 0 and 5;

(c) treating the compound formed in step (b) with a condensing agent under conditions permitting multiple macrolactamization so as to thereby form the composition.

DETAILED DESCRIPTION OF THE INVENTION

The present invention provides a composition of matter having the structure:

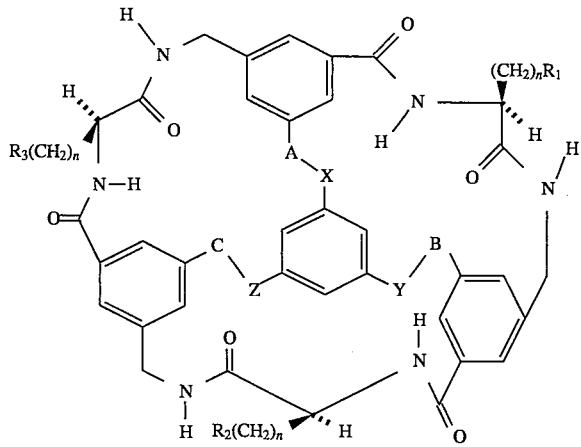

wherein each of A, B, C, X, Y, and Z is independently O, NH, $N(CH_2)_m CH_3$, $N(C=O)(CH_2)_m CH_3$, $CH_2$, S, or Se; each of $R_1$, $R_2$, and $R_3$ is independently phenyl, 4-hydroxyphenyl, pyridyl, pyrrolyl, indolyl, naphthyl, thiophenyl, $(C=O)(CH_2)_p CH_3$, $NH(C=O)(CH_2)_p CH_3$, OH, COOH, $NH_2$, or SH; and m, n, and p are integers between 0 and 5.

In one embodiment of the invention, X, Y, and Z are each O;

in another embodiment, they are each S. In certain other embodiments, $R_1$, $R_2$, and $R_3$ are each phenyl, or they are each 4-hydroxyphenyl. Additionally, in certain embodiments, n is desirably 1. The invention further provides a process of obtaining a purified enantiomeric isomer of a compound of interest from a mixture of isomers of such compounds which comprises contacting the mixture of isomers with the chiral host composition defined hereinabove under conditions such that the enantiomeric isomer binds to the composition to form a complex, separating the resulting complex from the mixture, treating the complex so as to separate the enantiomeric isomer from the composition, and recovering the purified enantiomeric isomer. In one embodiment, the process is used to purify enantiomers of amino acid derivatives, of which diamides are particularly effective.

The invention also provides a process of obtaining a purified organic compound of interest from a mixture of organic compounds able to form hydrogen bonds, which comprises contacting the mixture with the chiral host composition defined hereinabove under conditions such that the organic compound binds to he composition to form a complex, separating the resulting complex from the mixture, treating the complex so as to separate the compound from the composition, and recovering the purified compound. In one embodiment, the process is used to purify derivatives of amino acids differing in side-chains. The process is particularly well suited to purify diamide derivatives of amino acids.

One application of the composition is to bind it to a solid support such that a chromatographic adsorbent results which is specific for enantiomeric isomers of compounds of interest and other organic compounds of interest which differ only in side-chain substitution. Effective use of the composition bound to a solid support is made to obtain the enantiomeric isomers of an amino acid derivative in a purified form and to obtain a purified organic compound of interest able to form hydrogen bonds from a mixture of compounds. The compound to be purified by the composition is preferably a diamide.

The invention further provides a process of preparing the composition, which comprises:

(a) reacting a chiral multifunctional reagent containing at least one protecting group with a compound having the structure:

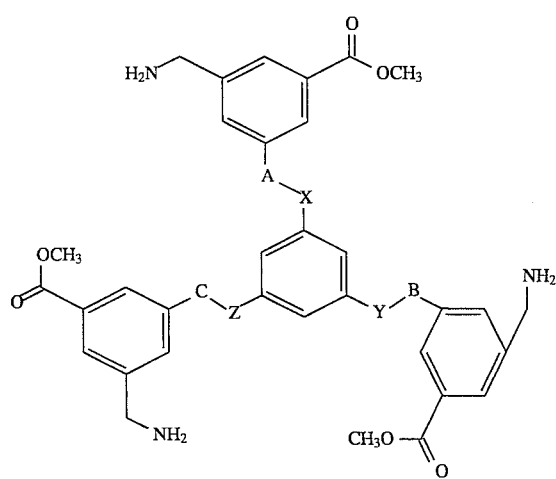

wherein each of A, B, C, X, Y, and Z is independently O, NH, $N(CH_2)_mCH_3$, $N(C=O)$ $(CH_2)_mCH_3$, $CH_2$, S, or Se, under condition permitting formation of a compound having the structure:

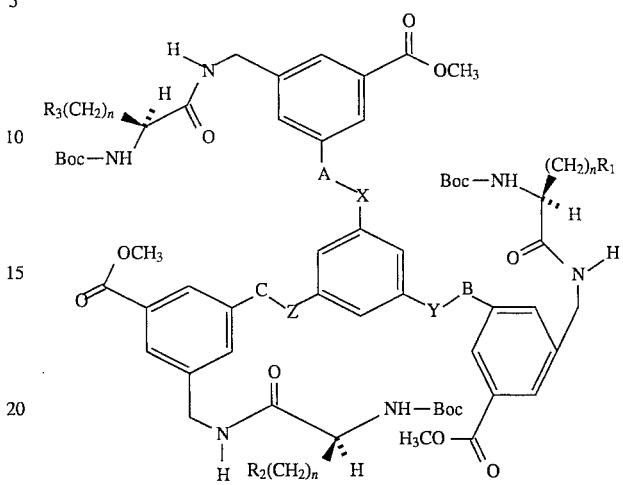

wherein each of A, B, C, X, Y, and Z is independently O, NH, $N(CH_2)_mCH_3$, $N(C=O)$ $(CH_2)_mCH_3$, $CH_2$, S, or Se; each of $R_1$, $R_2$, and $R_3$ is independently phenyl, 4-hydroxyphenyl, pyridyl, pyrrolyl, indolyl, naphthyl, thiophenyl, $(C=O)$ $(CH_2)pCH_3$, $NH(C=O)$ $(CH_2)_pCH_3$, OH, COOH, $NH_2$, or SH; and m, n, and p are integers between 0 n 5;

(b) treating the compound formed in step (a) under suitable conditions to cleave on protecting group to form a compound having the structure:

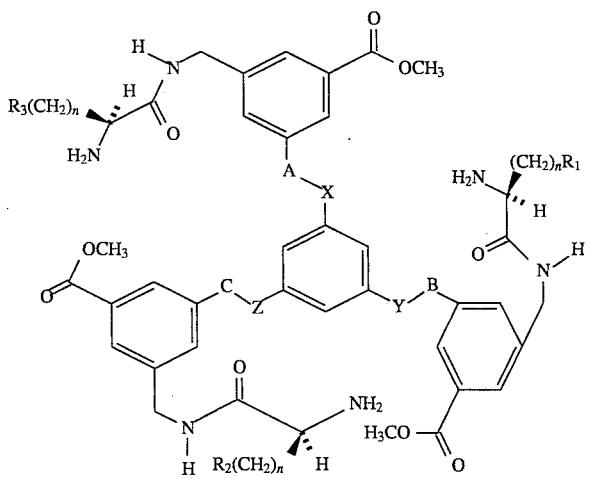

wherein each of A, B, C, X, Y, and Z is independently O, NH, $N(CH_2)_mCH_3$, $N(C=O)$ $(CH_2)_mCH_3$, $CH_2$, S, or Se; each of $R_1$, $R_2$, an $R_3$ is independently phenyl, 4-hydroxyphenyl, pyridyl, pyrrolyl, indolyl, naphthyl, thiophenyl, $(C=O)$ $(Ch_2)_pCH_3$, $NH(C=O)$ $(CH_2)_pCH_3$, OH, COOH, or SH; and m, n, and p are integers between 0 and 5;

(c) treating the compound formed in step (b) with a condensing agent under conditions permitting multiple macrolactamization, thereby forming the desired composition.

The preparation of the composition strategically exploits its $C_3$ symmetry. The synthesis of the composition could proceed in a manner analogous to the detailed experimental examples given hereinbelow for embodiments in which X, Y, and Z are S, and $R_1$, $R_2$, $R_3$ are 4-hydroxyphenyl, except that if there is only one protecting group in the chiral multifunctional reagent of step (a), then none of the side-group protection reactions would pertain.

The coupling of step (a) above can be carried out by several alternative methods of forming amide bonds. One approach is to contact the achiral tetraaromatic triamino triester above shown with the p-nitrophenyl active ester of the chiral multifunctional reagent, made from p-nitrophenol, N-hydroxybenzotriazole, and N,N-dicyclohexylcarbodiimide. The reaction may be performed in the presence of aprotic dipolar solvents, such as N,N-dimethylformamide, tetrahydrofuran, or dimethylsulfoxide, diluted with a miscible cosolvent, such as dichloromethane, to the extent required to achieve solubility of all reactants, at temperatures from about 0° to 100° C., preferably from 0° to 30° C. The preparation of the starting material for step (a) can be obtained by trialkylation of 1,3,5-trimercaptobenzene or phloroglucinol with N-protected methyl 3-(aminomethyl)-5-(bromomethyl)benzoate, followed by cleavage of the N-protecting group. In one embodiment of the invention, the chiral multifunctional reagent containing at least one protecting group in step (a) is an amino acid containing an N-protecting group. In certain embodiments, the amino acid is L-phenylalanine or L-tyrosine. The N-protecting group is preferably chosen such that it may be removed in process step (b) by an acid, for example, trifluoroacetic acid.

In general, process step (b) involves the removal of three protecting groups on the tetraaromatic intermediate. This reaction could be effected by any method corresponding to the lability of the protecting group. A large variety of protecting groups are available for the purpose, including t-butyloxycarbonyl (BOC), benzyloxycarbonyl, 2-bromobenzyloxycarbonyl, and p-toluensulfonyl. While a preferred method is to use acid-sensitive BOC groups, other effective protecting groups also removable by acid include biphenylisopropyloxycarbonyl (Bpoc) and adamantyloxycarbonyl (Adoc). Still other protecting groups may be selected such that alternative methods of removal are feasible according to the invention, including photolytic, reductive, electrochemical, and mild base conditions. This flexibility allows a wide range of chiral multifunctional reagents to be used to prepare the composition.

Prior to condensation process (c), the protecting ester group (for example, methyl) on each of the three aromatic moieties could be cleaved to give the carboxylic acid by (i) transesterification with trimethylsilylethanol, followed by (ii) fluoride-induced silane elimination. The condensing agent in step (c) could comprise a reagent generated (i) from an agent selected from a group comprising pentafluorophenol, hydroxybenzotriazole, 4-nitrophenol, 2-nitrophenol, pentachlorophenol, hydroxysuccinimide, and hydroxypiperidine and (ii) from an agent selected from a group consisting of N,N-dicyclohexyldiimide, diisopropylcarbodiimide, and carbonyldiimidazole. Other condensing methods may also serve the purpose, including Woodward's reagent K, mixed anhydrides, triphenylphosphine/2,2'-dipyridyl sulfide, ketenimines, and acyloxyphosphonium salts. In a preferred embodiment, the condensing agent is the combination of N,N-dicyclohexylcarbodiimide and pentafluorophenol. If the multifunctional chiral reagent of step (a) contains an alcohol function, the process of steps (b) and (c) could be simply adapted to generate three ester linkages after multiple macrolactonization. Other modifications in the multifunctional chiral reagent of step (a) could be readily envisioned to form such alternative linkages as thioesters, thionoesters, and phosphoramides.

The protecting groups which may be present on side-group functionalities could be cleaved by a method corresponding to their lability. In one embodiment, $R_1$, $R_2$, and $R_3$ are 4-hydroxyphenyl which should be made by coupling with the suitably protected multifunctional chiral reagent Boc-L-tyrosine (Tyr). The protecting group on the Tyr is preferably an allyl ether. The processes described provided the embodiments of the composition, wherein $R_1$, $R_2$, and $R_3$ are phenyl, in 30% overall yield for the trithia receptor and 7% yield for the trioxa receptor, respectively referred to hereinafter as 1 and 2. Preparation of the tyrosine trithia macrocycle is described in Examples 1 to 16, which serve as an ennabling model illustrative for all embodiments of the composition. Receptors 1 and 2 are capable of high binding selectivity among simple amino acid derivatives (Table I). With Boc-protected, N-methylamide acid derivatives, enantio-selectivity ranges from 1.7 to 3.0 kcal/mole with the L isomer always being bound preferentially (entries 1/2, 5/6, 7/8, 9/10, 12/13).

Side-chain functionality can also be distinguished by the chiral receptors (Table I; entries 1–8 vs 9, 10 and 12,13). The side-chain hydroxyls of serine and threonine contribute about 2 kcal/mole to association energies and effectively distinguish these amino acids from Ala, Val, and Leu. Such hydroxylated L-amino acid bind better than O-benzyl-L-serine (entry 11) by about 3 kcal/mole. Nuclear magnetic resonance data suggest that the operative mode of complexation involves close poximity of the C-terminal group of the amino acid derivatives to all four aromatic rings in the host. Entries 14–17 (Table I) suggest that other binding modes may apply to amino acid derivatives having small N-terminal functionalities such as acetyl.

The chiral host compounds may be utilized in any manner suitable for the intended purpose. For example, the host may be covalently bound to a polymer by modification of the synthetic method described above by replacing phloroglucinol or a similar starting material with one which has the additional substitution of an alkyl, aryl, or aralkyl, linker containing a reactive moiety at its terminus, comprising a halide, amine, carboxylate, alcohol, or thiol, if necessary in suitably protected form.

The resulting chiral polymer may serve as an adsorbent for use as a convenient extractive reagent, in which the polymer may be combined with a mixture of racemic amino acid derivatives or a mixture of compounds related by differing side-chain substitution in a range of polar or nonpolar solvents. After sufficient agitation at a temperature suitable for promoting binding of one component in the mixture, ranging from −90° to 180° C., preferably from 0° to 35° C. the, polymeric complex is then separated by gravity or suction filtration, centrifugation, or sedimentation and decanting. The desired enantiomeric derivative or related compound may be obtained by washing the polymer with a suitable buffer, solvent, or mixture of solvents at a temperature suitable for releasing the derivative from the polymeric host. The chiral polymer may also serve as an adsorbent in a chromatographic column, in which the mixture of enantiomers or related compounds may bind with different affinities, and then be eluted after washing with a suitable buffer, solvent, or mixture of solvents. The adsorbent is preferably prepared using finer meshes (>400 U.S. mesh) of chloromethylated 0.5–2.0% divinyl-benzene cross-linked polystyrene and either aminoethyl, hydroxyethyl, or carboxyethyl derivatives of phloroglucinol or benzenetrithiol, according to the described procedure. Any polymeric resin selected from the group consisting of polyacrylamide, phenolformaldehyde polymers, polymethacrylate, carbohydrates, aluminates, and silicates may serve as the solid medium.

The following Experimental Details are set forth to aid in an understanding of the invention, and are not intended, and should not be construed, to limit in any way the invention set forth in the claims which follow thereafter.

TABLE I

ΔG's of Association (kcal/mole) of 1 and 2 with Amino Acid Derivatives

| Entry | Peptide substrate | $-\Delta G^a$ | | Saturation$^b$ % | | $\Delta\Delta G^c$ | |
|---|---|---|---|---|---|---|---|
| | | 1 | 2 | 1 | 2 | 1 | 2 |
| 1 | N—Boc—D—Ala—NHMe | 1.7 | 2.1 | 53 | 70 | | |
| 2 | N—Boc—L—Ala—NHMe | 3.9 | 3.8 | 93 | 90 | 2.2 | 1.7 |
| 3 | N—Boc—L—Ala—NHBn | 1.4 | | 51 | | | |
| 4 | N—Boc—L—Ala—NHtBu | nc$^d$ | | | | | |
| 5 | N—Boc—D—Val—NHMe | 1.5 | 1.5 | 51 | 54 | | |
| 6 | N—Boc—L—Val—NHMe | 4.4 | 4.0 | 79 | 74 | 2.9 | 2.5 |
| 7 | N—Boc—D—Leu—NHMe | 1.5 | 1.6 | 64 | 60 | | |
| 8 | N—Boc—L—Leu—NHMe | 4.1 | 3.8 | 88 | 78 | 2.6 | 2.2 |
| 9 | N—Boc—D—Ser—NHMe | 3.8 | 4.4 | 86 | 94 | | |
| 10 | N—Boc—L—Ser—NHMe | >6.1 | >6.2 | 95 | 96 | >2.3 | >1.8 |
| 11 | N—Boc—L—Ser(OBn)—NHMe | 3.1 | | 83 | | | |
| 12 | N—Boc—D—Thr—NHMe | 3.2 | 3.6 | 84 | 90 | | |
| 13 | N—Boc—L—Thr—NHMe | >6.2 | lg$^e$ | >95 | | >3.0 | |
| 14 | N—Ac—D—Ala—NHMe | 2.7 | | 90 | | | |
| 15 | N—Ac—L—Ala—NHMe | 3.9 | | 94 | | 1.2 | |
| 16 | N—Ac—D—Ala—NHtBu | 2.0 | | 59 | | | |
| 17 | N—Ac—L—Ala—NHtBu | 3.0 | | 85 | | 1.0 | |

$^a$Measured by NMR titration at 25° C. with 1 or 2 at 0.5 mM concentration in CDCl$_3$.
$^b$Extent of extrapolated saturation at end of titration.
$^c$Enantioselectivity, ΔG(D) − ΔG(L).
$^d$No complexation detected.
$^e$Too large to measure accurately.

While not wishing to be bound by a particular theory of action, the high selectivity in the binding of various substrates to a host molecule as observed while practicing the present invention could result from high conformational homogeneity and substantial host/guest contact. Monte Carlo conformational searching using the MacroModel/ AMBER force field, in which Phe is modeled by Ala, predicts that the chiral receptors have similar conformations with C3 symmetry. The Phe's are folded into turns around the periphery of a large binding cavity with dimensions (~6 Å diameter) similar to those of α-cyclodextrin. Some variability remains in the central ring Ar-X-CH$_2$-Ar' torsion angles, with little effect on the shape and nature of the binding cavity. Experimental evidence supporting the predicted structure includes NH—CH$_a$ coupling constants (J(1)=8.1 Hz; J(2)=8.0 Hz) and N—H infrared bands (free and hydrogen-bonded: 3434,3321) cm$^{-1}$) in dilute CDCl$_3$ solution. The chiral host on forming a bound complex undergoes only minor conformational change, according to simulated annealing calculations. Specific contacts which may be responsible for the selective binding interactions in the complex could include three N—H/O=C hydrogen bonds, according to molecular mechanics modelling.

The chiral hosts of the present invention bind diamides of certain amino acids with high selectivity which is dependent upon the nature of the amino acid side chain (2~kcal/mol for serine vs alanine) and the identity of the N-alkyl substituent (>3 kcal/mol for methyl vs tert-butyl). These synthetic hosts are among the most enantioselective known, and bind certain derivatives of L-amino acids with selectivities as high as 3 kcal/mol. No other composition has been available to the art which achieves binding energy differentials of the magnitude herein disclosed for diastereoselective complexation of amino acid derivatives.

EXPERIMENTAL DETAILS

Example 1

Preparation of Methyl-3,5-dimethyl-benzoate

A solution of 3,5-dimethyl benzoic acid (25 g, 0.17 mol) in methanol (250 ml) was treated with sulfuric acid (1 ml, cat. amount) and heated to reflux. After 10 hours, the solution was cooled to room temperature, concentrated to approximately ½ volume and poured into 200 ml of crushed ice. The mixture was extracted twice with 200 ml portions of diethyl ether. The organic phase was extracted with saturated aqueous sodium carbonate, dried over magnesium sulfate, and concentrated under reduced pressure. The resulting solid was recrystallized from hexanes to yield the product (24.5 g, 90% yield) as volatile white plates. mp=32°–35° C. (lit. mp=35°–36° C.)

Example 2

Preparation of Methyl-3,5-bis(bromomethyl)-benzoate

A solution of methyl-3,5-dimethyl-benzoate (16.8 g, 0.10 mol) in carbon tetrachloride (150 ml) was treated with N-bromosuccinimide (35.6 g, 0.20 mmol), and benzoyl peroxide (500 mg, cat. amount), and heated to reflux. After 3 hours, the mixture was cooled to room temperature and filtered through a sintered glass funnel. The filtrate was concentrated under reduced pressure and recrystallized from diethyl ether/hexanes (1:1) to yield the product (18.0 g, 55% yield) as a granular white solid. mp 64°–70° C. (lit. mp 65°–69° C.); TLC (20% ethyl acetate/hexanes): R$_f$=0.65 (UV active, CAM stain)

Example 3

Preparation of Methyl-3-bromomethyl-5-bis(BOC)aminomethyl-benzoate

A mixture of sodiumhydride (3.6 g, 90mmol) and N,N-dimethylformamide (150 ml) was cooled to 0° C. and treated with solid di-tert-butyliminodicarboxylate (17.4 g, 76.0 mmol) with vigorous stirring. The mixture was stirred at 0° C. for 15 minutes, the ice bath was removed and a solution of methyl 3,5-bis(bromomethyl)-benzoate (23.6 g, 73.2 mmol) in N,N-dimethylform was added dropwise over 30 minutes. After 12 hours the mixture was poured into 100 ml ¼ saturated aqueous ammonium chloride and extracted with the three 100 ml portion of hexanes. The organic layer was dried over magnesium sulfate, concentrated under reduced pressure and chromatographed using a gradient of 10–20% ethyl acetate/hexanes to yield the product (22.0 g, 66% yield). TLC (20% ethyl acetate/hexanes): $R_f$=0.55 (UV active, CAM stain)

Example 4

Preparation of benzene-1,3,5-tris)methyl-3'-thiomethyl-5'-bis(BOC)aminomethyl-benzoate]

A solution of benzene-1,3,5-trithiol (900 mg, 5.16 mmol) in tetrahydrofuran (60 ml) was treated with N,N-diisopropylethylamine (3.1 ml, 17.67 mmol) with vigorous stirring. The mixture was allowed to stir until all solids had dissolved and was treated with solution of methyl-3-bromomethyl-5-bis(BOC)aminomethyl-benzoate (8.1 g, 17.67 mmol) in tetrahydrofuran. After 24 hours the mixture was poured into 100 ml saturated aqueous ammonium chloride and extracted with three 100 ml portions of diethyl ether. The organic phase was dried over magnesium sulfate, concentrated under reduced pressure, and the resulting oil was chromatographed using a gradient of 20–40% ethyl acetate/hexanes to yield the product (5.10 g, 76% yield) as a colorless oil. TLC (40% ethyl acetate/hexanes ): $R_f$=0.65 (UV active, Cl$_2$/TDM stain)

Example 5

Preparation of benzene-1,3,5-tris[methyl-3'-thiomethyl-5'-aminomethyl-benzoate hydrochloride salt]

A solution of benzene-1,2,3,5-tris[methyl-3'-thiomethyl-5'-bis(BOC)aminomethyl-benzoate hydrochloride](4.8 g, 3.67 mmol) in absolute methanol (25 ml) was treated with 25 ml "10% methanolic HCl" (a mixture of 2.5 ml acetyl chloride and 22.5 ml absolute methanol) and allowed to stir at room temperature for 3 hours. All volatiles were removed under reduced pressure and the resulting white powder was dried under high vacuum. The product (3.00 g, quant. yield) was used without additional purification.

Example 6

Preparation of N-α-BOC-L-tyrosine methyl ester

A solution of L-tyrosine methyl ester hydrochloride (10.0 g, 43.2 mmol) in N,N-dimethylformamide (100 ml) was cooled to 0° C. and treated with solid di-tert-butyl dicarbonate (13.0 g, 65 mmol) and triethylamine (6.6 ml, 47.5 mmol). After one hour the ice bath was remove and the solution was allowed to warm to room temperature. After 4 hours the solution was poured into 200 ml ethyl acetate, extracted with 100 ml 1.0M aqueous hydrochloric acid, 200 ml saturated aqueous sodium bicarbonate, 200 ml saturated aqueous sodium chloride, dried over magnesium sulfate, and concentrated under reduced pressure. The crude product (12.56 g, 98% yield) was used without additional purification.

Example 7

Preparation of N-α-BOC-L-tyrosine-O-allyl ether methyl ester

A solution of N-α-BOC-L-tyrosine methyl ester (12.5 g, 42.3 mmol) in N,N-dimethylformamide (100 ml) was treated with allyl bromide (4.5 ml, 51.8 mmol), tetra-n-butylammonium iodide (1.5 g, 4.3 mmol) and potassium carbonate (12 g, 86.4 mmol) and allowed to stir overnight. After 14 hours the mixture was poured into 200 ml ethyl acetate and extracted with 100 ml 1.0 M aqueous citric acid, 100 ml saturated aqueous sodium bicarbonate, saturated aqueous sodium chloride, dried over magnesium sulfate and concentrated under reduced pressure. The resulting oil was chromatographed using a gradient of 20–40% ethyl acetate/hexanes to yield the product (14.0 g, 99% yield) a colorless oil. TLC (40% ethyl acetate/hexanes): $R_f$=0.40 (UV active, Cl$_2$/TDM stain)

Example 8

Preparation of N-α-BOC-L-tyrosine-O-allyl ether

A solution of N-α-BOC-L-tyrosine-O-allyl ether methyl ester (14.0 g, 41.7 mmol) in a mixture of tetrahydrofuran (100 ml) and water (10 ml) was treated with lithium hydroxide (10.0 g, 260 mmol) and allowed to stir at room temperature. After 6 hours all of the starting material had been consumed, as determined by thin layer chromatography, and the reaction mixture was diluted with 200 ml ethyl acetate and acidified to pH 2 with 1.0M aqueous potassium hydrogen sulfate. The organic phase was dried over magnesium sulfate and concentrated under reduced pressure to yield the product (13.4 g, quant. yield). The product was used without additional purification.

Example 9

Preparation of N-α-BOC-L-tyrosine-O-allyl ether-p-nitrophenyl ester

A solution of N-α-BOC-L-tyrosine-O-allyl ether (13.4 g, 41.7 mmol) in chloroform (100 ml) was cooled to 0° C. and was treated with p-nitrophenol (17 g, 128 mmol), N-hydroxy-benzotriazole (3.0 g, 21.3 mmol) and N, N'-dicyclohexylcarbodiimide (10.5 g, 51.2 mmol). The mixture was allowed to stir overnight at room temperature. After 15 hours the solution was filtered to remove N,N'-dicyclohexylurea, concentrated under reduced pressure and chromatographed using 100% chloroform to yield the product (13.7 g, 74% yield) as a yellow oil which solidified upon standing. TLC (100% chloroform): $R_f$=0.30 (UV active, ninhydrin stain)

Example 10

Preparation of benzene-1,3,5-tris[methyl-3'-thiomethyl-5'-aminomethy-(N-α-BOC-L-tyrosine-amide-O-allyl-ether-)benzoate]

A solution of benzene-1,3,5-tris[methyl-3'-thiomethyl-5'-aminomethyl-benzoate hydrochloride salt](2.33 g, 2.86 mmol) in N,N-dimethylformamide (30 ml) was treated with N,N-diisopropylethylamine (1.9 ml, 10.87 mmol) with vigorous stirring until all solids had dissolved. The solution was cooled to 0° C. and treated with solid N-α-BOC-L-tyrosine-O-allyl-ether-p-nitrophenyl ester (2(0(4.3 g, 9.72 mmol). After one hour the ice bath was removed and the mixture was mixed with silica gel (13 g) and all volatiles were removed under reduced pressure. The pre-absorbed reaction mixture was placed directly onto a chromatography column containing silica gel equilibrated with 40% ethyl acetate/hexanes. The column was eluted with 40% ethyl acetate/hexanes to remove unreacted p-nitrophenyl ester and most of the p-nitrophenol. The product was then eluted with 10% methanol/chloroform to yield a fine yellow powder slightly contaminated with p-nitrophenol. The mixture was redissolved in methylene chloride and extracted with two 200 ml portions of 0.5M aqueous sodium hydroxide. The organic phase was dried over magnesium sulfate and concentrated under reduced pressure to yield to product (4.41 g, 96% yield) as a pale yellow powder. TLC (8% acetone/methylene chloride): $R_f$= 0.45 (UVactive, $Cl_2$/TDM stain)

Example 11

Preparation of benzene-1,3,5-tris[2"-(trimethyl)silylethyl-3'-thiomethyl-5'-aminomethyl-(N-α-BOC-L-tyrosine-amide-O-allyl-ether)-benzoate]

A suspension of benzene-1,3,5-tris[methyl-3'-thiomethyl-5'-aminomethyl-(N-α-BOC-L-tyrosine-amide-O-allyl-ether)-benzoate] (4.3 g, 2.66 mmol) in 2-(-trimethyl)silylethanol (10 ml, 70 mmol) and toluene (10 ml) was thoroughly purged with argon and treated with titanium ethoxide (0.050 ml, catalytic amount) and heated to reflux. After 6 hours the mixture was cooled to room temperature, filtered through a pad of Celite (diatomaceous earth) and concentrated under reduced pressure. The resulting oil was chromatographed using a gradient of 100% methylene chloride-5% methanol/methylene chloride to yield the product (4.2 g, 84% yield) as a pale yellow powder. TLC (8% acetone/methylene chloride): $R_f$=0.85 (UV active, $Cl_2$/TDM stain)

Example 12

Preparation of benzene-1,3,5-tris[3'-thiomethyl-5'-aminomethyl-(N-α-BOC-tyrosine-amide-O-allyl-ether)-benzoic acid]

A solution of benzene-1,3,5-tris[2'-(trimethyl)silylethyl-3'-thiomethyl-5'-aminomethyl-)N-α-BOC-L-tyrosine-amide-O-allyl-ether)-benzoate](4.2 g, 2.24 mmol) in tetrahydrofuran (75 ml) was treated with tetra-n-butylammoniumfluoride (1.0M solution in tetrahydrofuran) (10.08 ml, 10.08 mmol). After 4 hours the solution was diluted with 100 ml ethyl acetate and acidified to pH 2 with 1.0M aqueous potassium hydrogen sulfate. The organic layer was dried over magnesium sulfate and concentrated under reduced pressure to yield the product (3.50 g, quant. yield). The product was used without additional purification. TLC (10% methanol/chloroform): $R_f$=0.15 (UV active, $Cl_2$/TDM stain)

Example 13

Preparation of benzene-1,3,5-tris[pentalorophenyl-3'-thio-methyl-5'-aminomethyl- (N-α-BOC-L-tyrosine-amide-O-allyl -ether)-benzoate]

A solution of benzene-1,3,5-tris[3'-thiomethyl-5'-aminomethyl-(N-α-BOC-L-tyrosine-amide-O-allyl-ether)-benzoic acid](3.50 g, 2,24 mmol) in tetrahydrofuran (50 ml) was treated with pentafluorophenol (3.7 g, 20.16 mmol), and was allowed to stir at room temperature. After 3 hours the reaction mixture was concentrated under reduced pressure and the resulting oil was chromatographed using a gradient of 100% methylene chloride-10% acetone/methylene chloride to yield the product (2.60 g, 56% yield) as a white powder. TLC (5% acetone/methylene chloride): $R_f$=0.45 (UV active, CAM stain)

Example 14

Preparation of benzene-1,3,5-tris[{pentafluorophenyl-3'-thio-methyl-5'-aminomethyl-(L-tyrosine-amide-O-allyl-ether)-bezoate}-trifluoroacetate salt]

A solution of benzene-1,3,5-tris[pentafluorophenyl-3'-thio-methyl-5'-aminomethyl-(N-α-BOC-L-tyrosine-amide-O-allyl-ether)-benzoate] (2.5 g, 1.21 mmol) in methylene chloride (100 ml) was treated with anisole (10.0 ml, 93.0 mmol) and trifluoroacetic acid (50.0 ml). After 3 hours the mixture was concentrate under reduced pressure, resuspended in toluene and concentrated again. Finally, the product was triturated three times in diethyl ether to yield the product (1.90 g, quant. yield) as a white powder. The product was used without additional purification.

Example 15

Preparation of L-tyrosine macrocycle tris-allyl ether

A solution of benzene-1,3,5-[{pentafluorophenyl-3'-thio-methyl-5'-aminomethyl-(L-tyrosine-amide-O-allyl-ether)-benzoate}-trifluoroacetate salt] (1.47 g, 1.21 mmol) in N,N-dimethylacetamide (25 ml) was added via syringe pump (33 hours) to a stirring solution of N,N-diisopropylethylamine (30.0 ml, 180 mmol) in tetrahydrofuran (500 ml). Twelve hours after the addition had been completed, the reaction mixture was diluted with an equal volume of ethyl acetate, extracted with two 200 ml portion of 5% aqueous hydrochloric acid, two 200 ml portions of saturated aqueous sodium bicarbonate, and 100 ml saturated aqueous sodium chloride. The organic phase was dried over magnesium sulfate, concentrated under reduced pressure and chromatographed using a gradient of 100% chloroform —5% methanol/chloroform to yield the product (892 mg, 65% yield) as a pale yellow powder. TLC (25% acetone.methylene chloride): $R_f$=0.45 (UV active, CAM stain)

Example 16

Preparation of the L-tyrosine macrocycle

A solution of the L-tyrosine macrocycle tris-allyl ether (50 mg, 0.041 mmol) in tetrahydrofuran (15 ml) was treated with 5,5-dimethyl-cyclohexan-1,3-dione (100 mg, 0.71 mmol) and tetrakis-(triphenylphosphine)palladium (10.0 mg, cat. amount) and allowed to stir at room temperature. After 4 hours the solution was diluted with 50 ml ethyl acetate and extracted with three 20 ml portions of saturated aqueous sodium bicarbonate and 20 ml saturated aqueous sodium chloride. The organic phase was dried over magnesium sulfate and concentrated under pressure. The resulting solid was chromatographed using 10% methanol/chloroform to yield the product (40.0 mg, 89% yield) as a pale yellow powder. TLC (10% methanol/chloroform): $R_f$=0.20 (UV active, CAM stain)

Example 17

Preparation of a Receptor Bound to a Solid Support

A solid phase peptide reaction vessel was charged with Merrifield resin (chloromethylated polystyrene cross-linked with 2% divinylbenzene; 100 mg, 0.100 meq), the macrocyclic tris-phenol made according to Example 16 (110.0 mg, 0.100 mmol), potassium carbonate (14 mg, 0.100 mmol), and N,N-dimethylformamide (2 ml). The mixture was placed on a rotary agitator for four days. The reaction mixture was washed successively with 5×5 ml portions of methylene chloride, methanol, deionized water, methanol, and methylene chloride. The resulting solid was dried under high vacuum and weighed to determine the amount of alkylation. The coupled resin weighed 116.3 mg (approximately 15% based on chloromethyl groups). The organic washes were diluted with 100 ml ethyl acetate and extracted with 50 ml portions of 1 M aqueous potassium hydrogen sulfate, saturated aqueous sodium bicarbonate, and saturated aqueous sodium chloride. The organic phase was dried over magnesium sulfate, concentrated under reduced pressure, and chromatographed using 10% methanol/chloroform to recover unreacted tris-phenol (40.1 mg). The infrared spectrum shows type I, II, and III amide bands (1650, 1510, and 1230 cm$^{-1}$).

Example 18

Method of Resolution of N-α-BOC-DL-Valine Methylamide

The resin-bound tyrosine receptor (50 mg) prepared in Example 17 was placed in a solid-phase peptide synthesis reaction vessel (a cylinderical glass container with a ground glass Joint (standard taper 14/20) on top, a coarse glass frit, and a stopcock at the bottom; treated with dichlorodimethylsilae to reduce adhesion to the glass surface) was pre-selled by washing 5 times with 50 ml portions of chloroform and forcing excess solvent out with a stream of argon. A solution of 10 mM N-α-BOC-DL-valine methylamide (57.6 mg) was dissolved in perdeuterobenzene, and incubated with the resin-bound host for five minutes. The resin was washed with acetone (5 times 50 ml). The collected washings were concentrated under reduced pressure to afford 14.5 mg of resolved N-α-BOC-valine methylamide. The extent of enantiomeric enrichment was determined as follows: The BOC group was removed by treatment with a large excess of anhydrous methanolic HCl. On neutralization with triethylamine, the resulting amine was reacted with N-α-BOC-L-alanine p-nitrophenyl ester to give N-α-BOC-L-alanylvaline methylamide (19.0 mg, 97.2%) after chromatography. NMR integration and comparison with authentic DL diastereomeric compounds revealed an 85:15 mixture of diastereomers, i.e., 70% enantiomeric enrichment. The resin could be regenerated by washing five times with 50 ml portions of methanol, dried under a stream of argon, and re-swelled with chloroform.

What is claimed is:

1. A method of obtaining a purified organic compound of interest from a mixture of organic compounds, which comprises contacting the mixture with a composition having the structure:

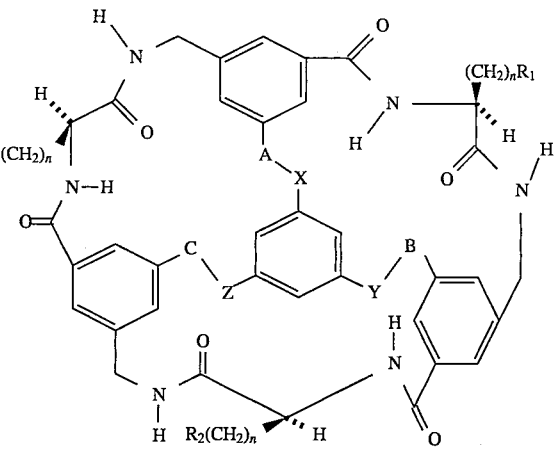

wherein each of A, B, C, X, Y, and Z is independently O, NH, N(CH$_2$)$_m$CH$_3$, N(C=O) (CH$_2$)$_m$CH$_3$, CH$_2$, S, or Se; each of R$_1$, R$_2$, and R$_3$ is independently phenyl, 4-hydroxyphenyl, pyridyl, pyrrolyl, indolyl, naphthyl, (C=O) (CH$_2$)$_p$CH$_3$, NH(C=O) (CH$_2$)$_p$CH$_3$, OH, COOH, NH$_2$, or SH; and m, n, and p are integers between 0 and 5, so that the organic compound of interest binds to the composition to form a complex, separating the resulting complex from the mixture, treating the complex so as to separate the organic compound from the composition, and recovering the purified organic compound of interest.

2. The method of claim 1, wherein the purified organic compound of interest is an amino acid derivative.

* * * * *